(12) United States Patent
Ginggen et al.

(10) Patent No.: US 7,720,546 B2
(45) Date of Patent: May 18, 2010

(54) DUAL POWER SUPPLY SWITCHING CIRCUITRY FOR USE IN A CLOSED SYSTEM

(75) Inventors: Alec Ginggen, Plymouth, MA (US); Rocco Crivelli, Bellinzona (CH)

(73) Assignee: Codman Neuro Sciences Sárl, Le Locle (CH)

( * ) Notice: Subject to any disclaimer, the term of this patent is extended or adjusted under 35 U.S.C. 154(b) by 652 days.

(21) Appl. No.: 10/955,678

(22) Filed: Sep. 30, 2004

(65) Prior Publication Data
US 2006/0069412 A1 Mar. 30, 2006

(51) Int. Cl.
*A61N 1/08* (2006.01)
(52) U.S. Cl. .......................... 607/61; 607/33
(58) Field of Classification Search ............... 128/908; 607/33, 61, 63
See application file for complete search history.

(56) References Cited

U.S. PATENT DOCUMENTS

| | | | |
|---|---|---|---|
| 4,041,954 A | 8/1977 | Ohara | |
| 4,082,097 A * | 4/1978 | Mann et al. | 607/33 |
| 4,793,353 A | 12/1988 | Borkan | |
| 5,314,453 A | 5/1994 | Jeutter et al. | |
| 5,733,313 A | 3/1998 | Barreras, Sr. et al. | |
| 5,894,413 A | 4/1999 | Ferguson et al. | |
| 6,400,991 B1 | 6/2002 | Kung | |
| 6,445,956 B1 | 9/2002 | Laird et al. | |
| 6,456,883 B1 * | 9/2002 | Torgerson et al. | 607/34 |
| 7,212,110 B1 * | 5/2007 | Martin et al. | 340/539.12 |

FOREIGN PATENT DOCUMENTS

EP 1 107 437 6/2001

* cited by examiner

*Primary Examiner*—Carl H. Layno
*Assistant Examiner*—Tammie K Helelr
(74) *Attorney, Agent, or Firm*—Cheryl F. Cohen, LLC

(57) ABSTRACT

Optimal power switching circuitry for use in a closed system such as a TET system including an internal device separated from an external device by a boundary. The internal and external devices being powered by separate power sources. During telemetric communication from the external device to the internal device an external RF energy source is produced. If the power supplied by the external RF energy source produced during communication from the external device to the internal device exceeds that required for powering of the internal device, then the power switching circuitry cuts off power to the internal power source and instead draws power from the external RF energy source thereby conserving power consumed from the internal power source. The power switching circuitry may be implemented using either passive components (e.g., diodes) or active components (e.g., an analog switch).

10 Claims, 4 Drawing Sheets

DUAL POWER SUPPLY SWITCHING CIRCUITRY FOR USE IN A CLOSED SYSTEM

BACKGROUND OF THE INVENTION

1. Field of the Invention

The present invention is directed to a closed system such as a transcutaneous energy transfer (TET) system and, in particular, to a dual power supply switching system for a TET system wherein powering of an implantable medical device and its associated components is switched, during communication from the external device to the implant, between an internal power source of the implantable medical device and an external RF power source produced by the external device.

2. Description of Related Art

In a variety of scientific, industrial, and medically related applications, it may be desirable to transfer energy or power (energy per unit time) across some type of boundary. For example, one or more devices that require power (e.g., electrical, mechanical, optical, and acoustic devices) may be located within the confines of a closed system, or "body," in which it may be difficult and/or undesirable to also include a substantial and/or long term source of power. The closed system or body may be delimited by various types of physical boundaries, and the system internal to the boundary may be living or inanimate, may perform a variety of functions, and may have a variety of operational and physical requirements and/or constraints. In some cases, such requirements and constraints may make the implementation of a substantial and/or long term "internal" power source for internally located devices problematic.

In some closed systems, repeated entry into the system may be undesirable for a variety of reasons. In other closed systems, significant internal power requirements and a limited internal space may prohibit the implementation of a suitably sized internal power source. In yet other systems, contamination and/or security issues may pose particular challenges in implementing an internal power source. For any combination of the foregoing and other reasons, a power source external to the system and some feasible means of transferring power from the external source to one or more internal devices may be preferable in some applications.

One common example of a closed system is the human body. In some medically related and scientific applications, a variety of prosthetic and other medical devices that require power may be surgically implanted within various portions of the body. Some examples of such devices include, but are not limited to, drug infusion pumps, pacemakers, defibrillators, cochlear implants, sensors and stimulators. With respect to the human body, issues such as repeated reentry or surgery, internal space limitations, and contamination (e.g., infection) are factors to consider when selecting a suitable internal power source for some of these implantable medical devices.

Accordingly, in some medical implant applications, "transcutaneous energy transfer" (TET) devices are employed to transfer energy from outside the body to inside the body, to provide power to one or more implanted prostheses or devices from an external power source. One example of a conventional TET device is a transformer that includes a primary winding (or coil) external to the body and a secondary winding internal to the body. Both the primary and secondary windings generally are placed proximate to respective outer and inner layers of a patient's skin; hence, the term "transcutaneous" commonly refers to energy transfer "through the skin." Energy is transferred from the primary winding to the secondary winding in the form of an RF field.

In a system employing an implantable medical device and external control unit each of the implantable medical device and external control unit preferably has its own power source, e.g., a battery, for powering its associated circuitry and its associated components. The implantable medical device battery, regardless of whether primary/non-rechargeable or secondary/rechargeable, has a limited lifespan and a predetermined amount of energy or power before having to be replaced or recharged.

It is therefore desirable to develop and an improved TET system having circuitry for optimally switching from an internal power source to an external RF power source so as to reduce the energy consumed from the internal power source associated with the implant.

SUMMARY OF THE INVENTION

The present invention is directed to TET system that includes circuitry for optimally switching from an internal power source to an external RF power source.

The present invention is directed to TET system that minimizes power consumption of the implantable medical device power source.

One aspect of the invention relates to a closed system such as a TET system having dual power supply switching circuitry. The system includes an internal device disposed interior of a boundary and powered by an internal power source. Disposed separated from the internal device and exterior to the boundary is an external device. The external device is in telemetric communication with the internal device and generates an external RF energy source during telemetric communication with the internal device. Power switching circuitry is used to switch from the internal power source to the external RF energy source during communication from the external device to the internal device when power supplied by the external RF energy source exceeds that required for powering the internal device.

Yet another aspect of the present invention is directed to a method for operating the dual power supply switching circuitry in the system described above. Specifically, the method is realized by generating during communication of the external device with the internal device an external RF energy source. During communication from the external device to the internal device when power supplied by the external RF energy source exceeds that required for powering the internal device, powering of the internal device is switched from the internal power source to the external RF energy source using power switching circuitry.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which:

FIG. 2b is an exemplary flow diagram of the passive power switching circuitry of FIG. 2a;

FIG. 3b is an exemplary flow diagram of the active power switching circuitry of FIG. 3a.

DETAILED DESCRIPTION OF THE INVENTION

Figure 1:
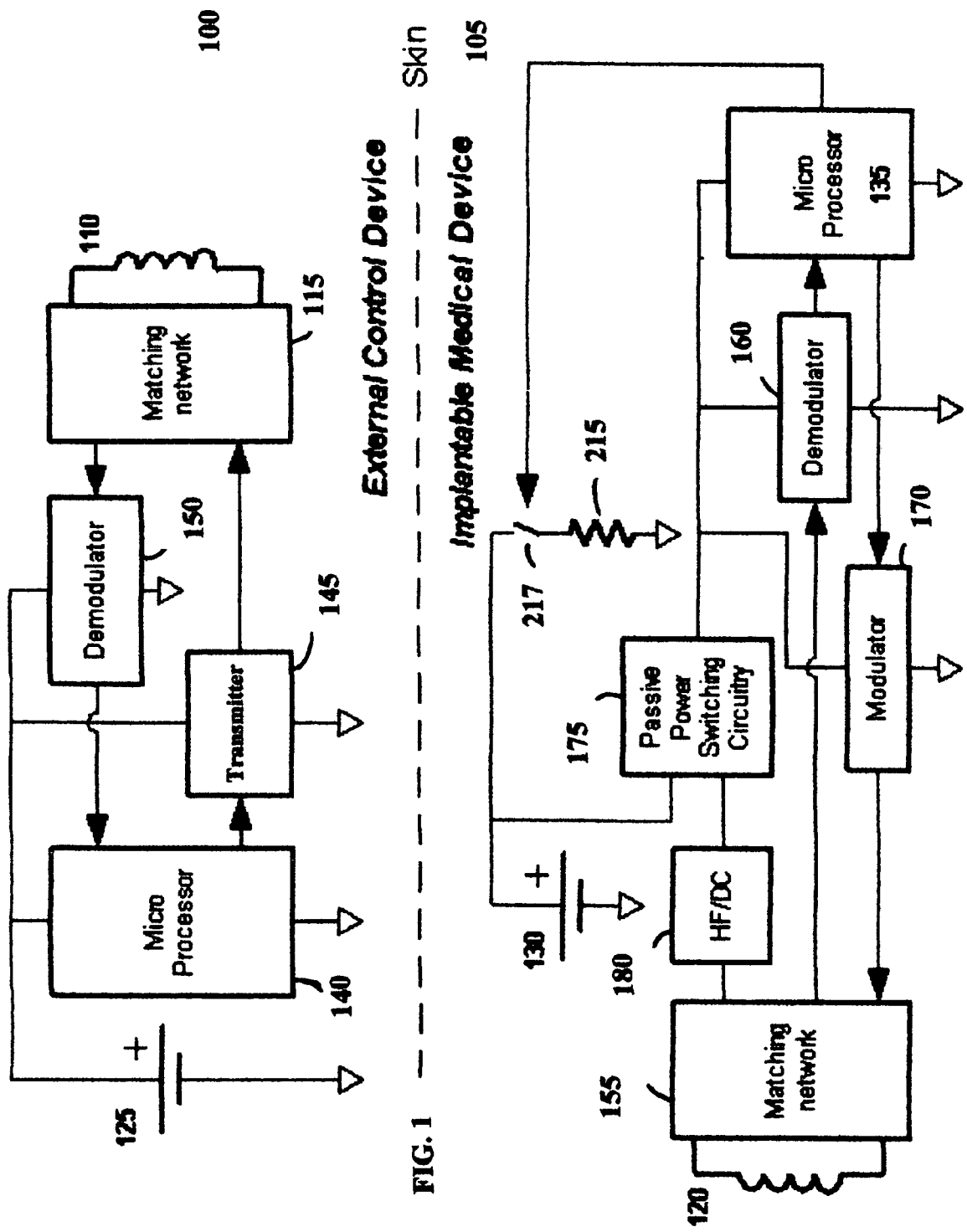
FIG. 1 is a schematic diagram of an exemplary TET system in accordance with the present invention including an external device in telemetric communication with an implantable medical device, wherein the implantable medical device employs passive power switching circuitry.

The present invention is directed to an energy efficient closed system such as a TET system that includes a first internal electronic device in telemetric communication with and separated by a physical boundary by a second external electronic device, wherein each electronic device has its own power source (e.g., battery). By way of example, the TET system and method in accordance with the present invention is shown in FIG. 1 for an implantable drug infusion pump in telemetric communication with an external device, e.g., a control unit or PC. It is to be understood, however, that the present invention may be used for other implantable medical devices or other electronic devices not related to the medical field. The present invention is suitable for any closed system comprising two electronic devices that communicate via telemetric link, wherein the energy used to power the internal device is optimally switched from an internal power source to an external RF source produced by the external device during communication with the internal device.

The exemplary TET system shown FIG. 1 comprises an external device 100 (e.g., a control unit) in telemetric communication with an implantable medical device 105 (e.g., an implantable drug infusion pump). External device 100 includes a primary coil 110 connected to a tuned matching network or circuit 115. A demodulator 150 is connected to the matching network 115 and demodulates the data signal from the received carrier signal. In turn, the demodulator 150 is electrically connected by a microprocessor or controller 140. A transmitter 145 is connected between the microprocessor 140 and matching network 115. All components and circuitry associated with the external device 100 are powered by a primary power source 125. In a preferred embodiment, the power source 125 for powering the external device and its associated circuitry and components is a secondary/rechargeable battery, most preferably a smart rechargeable battery.

The implantable medical device 105 has an associated secondary coil 120 connected to tuned a matching network or circuit 155. A demodulator 160 is connected to the matching network 155 for extracting the data signal from the received carrier signal. Microprocessor 135 is, in turn, connected to the demodulator 160. Electrically connected between the microprocessor 135 and matching network 155 is a modulator 170 for modulating the signal prior to transmission to the external device 100. A secondary or internal power source 130 provides power to all the components and circuitry associated with the implantable medical device. Sometimes the implantable medical device 105 such as an implantable drug infusion pump remains continuously active at all times to maintain operation of the components and circuitry associated therewith. In such applications, the secondary power source 130 is preferably a primary/non-rechargeable battery.

Heretofore, the components and circuitry of the implantable medical device 105 have been powered exclusively by its associated internal power source 130, e.g., battery. During telemetric communication from the external device 100 to the implantable medical device 105 an RF field is generated. This external RF energy source may be used as an alternative source for providing power needed by the implantable medical device 105 and associated circuitry to operate which would otherwise be drawn from the internal battery 130 associated with the implantable medical device. Accordingly, the implantable medical device 105 in accordance with the present invention has been designed to include a high frequency-to-DC converter (HF/DC) 180 and passive power switching circuitry 175 to optimally switch powering of the implantable medical device 105 and its associated components and circuitry from the internal power source 130 to the external RF energy source. Switching between power sources should preferably be instantaneous, automatic and relatively smooth.

Figure 2A:
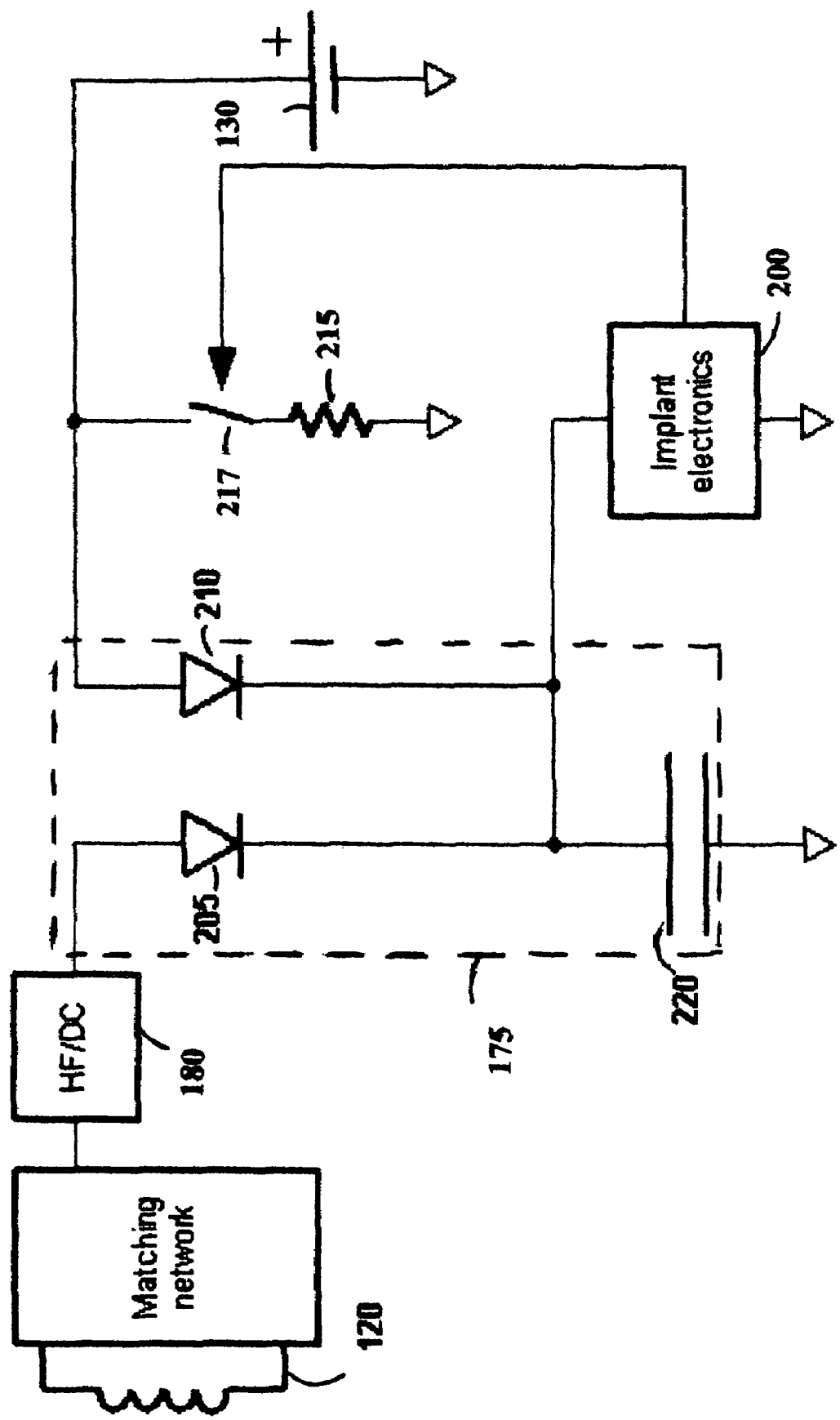
FIG. 2a is a schematic diagram of exemplary passive power switching circuitry in FIG. 1.
Figure 2B:
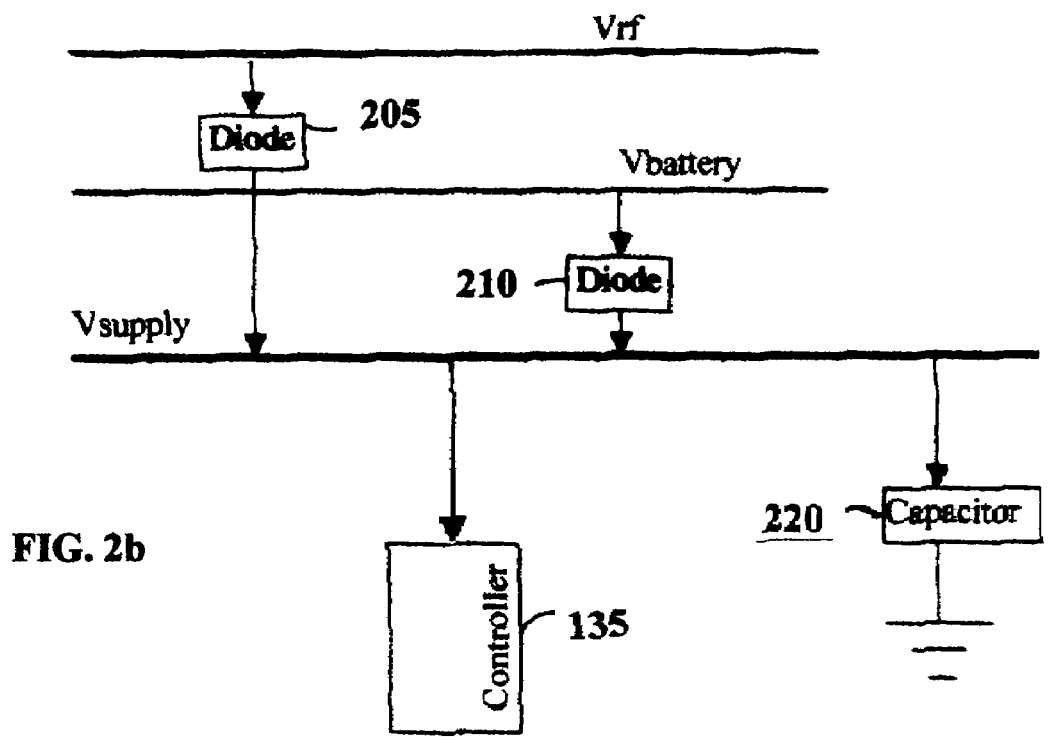

FIGS. 2a & 2b represent schematic and flow diagrams, respectively, of exemplary passive power switching circuitry 175 of FIG. 1 using diodes. By way of example, power switching circuitry 175 is used to switch between an internal battery source 130 associated with the implantable medical device 105 and an external RF energy source emitted by an external device 100 during communication with the implantable medical device. In FIG. 2a, demodulator 160, microprocessor 135 and modulator 170 are generically represented by implant electronics 200. Despite not being shown, the implantable medical device may include additional components as part of the implant electronics 200 depending on the particular functionality of the implant device. For example, an implantable drug infusion pump may include circuitry for controlling the opening and closing of the valve to the reservoir in which the medication is stored.

A first diode 205 is electrically connected between the voltage supply line (Vsupply) and the RF voltage (Vrf), while a second diode 210 is connected between the voltage supply line (Vsupply) and the battery voltage (Vbattery). A capacitor 220 is connected to the voltage supply line (Vsupply) and serves as the stopgap energy supplier during switching of the power supply between Vbattery and Vrf to prevent any interruption in communication.

Typically, the components when powered by the internal battery utilize substantially all the energy in the battery. By way of example, the implantable components may require a minimum of approximately 1.8 V and a maximum of approximately 3.6 V to operate, while the battery voltage is selected to be approximately 2.8 V when fully charged and drops to approximately 1.8 V towards the end of life of the battery. However, a forward voltage drop is experienced across the diode. This drop in voltage will reduce the full range of the battery that is able to power the components. In designing the power switching circuitry it is desirable to select a diode such as a Schottky diode having a relatively low voltage drop, preferably approximately 0.2 V to approximately 0.4 V. Due to the forward voltage drop across the diode the components will operate between approximately 2.8 V and approximately 2.1 V (minimum working voltage of approximately 1.8 V+diode forward voltage drop (e.g., approximately 0.3 V)). Once the battery voltage falls below approximately 2.1 V (minimum working voltage of approximately 1.8 V+the forward voltage drop (e.g., approximately 0.3 V)) the battery will not be able to supply the voltage needed to operate the components. Thus, the full battery range capable of powering the components is reduced by the forward voltage drop across the diode.

In operation, during communication of the external device 100 with the implantable medical device 105, if the power supplied by the external RF energy source exceeds that required to energize the implantable medical device and its associated components, then the second diode 210 is reverse biased and all power is drawn from the external RF power source. When power is drawn from the external RF energy source, a backward or reverse leakage current is exhibited in diode 210 which is detrimental to the battery 130. To circumvent this potentially damaging effect on the battery, a leakage current path is created via a switch 217 connected in series to a resistor 215 whose resistance is lower than that of the battery 130. In the presence of an external RF voltage, switch 217 is closed so that the leakage current flows through the resistor 215 rather than the battery 130.

On the other hand, whenever there is no RF communication or the RF energy emitted during communication from the external device 100 to the implantable medical device 105 is less than or equal to that required to energize the implantable medical device and its associated components, the first diode 205 is reverse biased and all components in the implantable medical device draw power from the battery 130. Thus, switching of the power source used to energize the implantable medical device and its associated components from the battery to the external RF energy source emitted by the external device during communication with the implant will occur only when the power supplied by the emitted RF field exceeds that required to energize the implantable medical device and its associated components. Substantially all the battery potential is typically consumed by the components and associated circuitry of the implantable medical device when powered by the battery 130. Under such circumstances, switching from the internal power source 130 to the external RF power source will take place only when the external RF voltage potential exceeds the battery voltage.

Figure 3A:
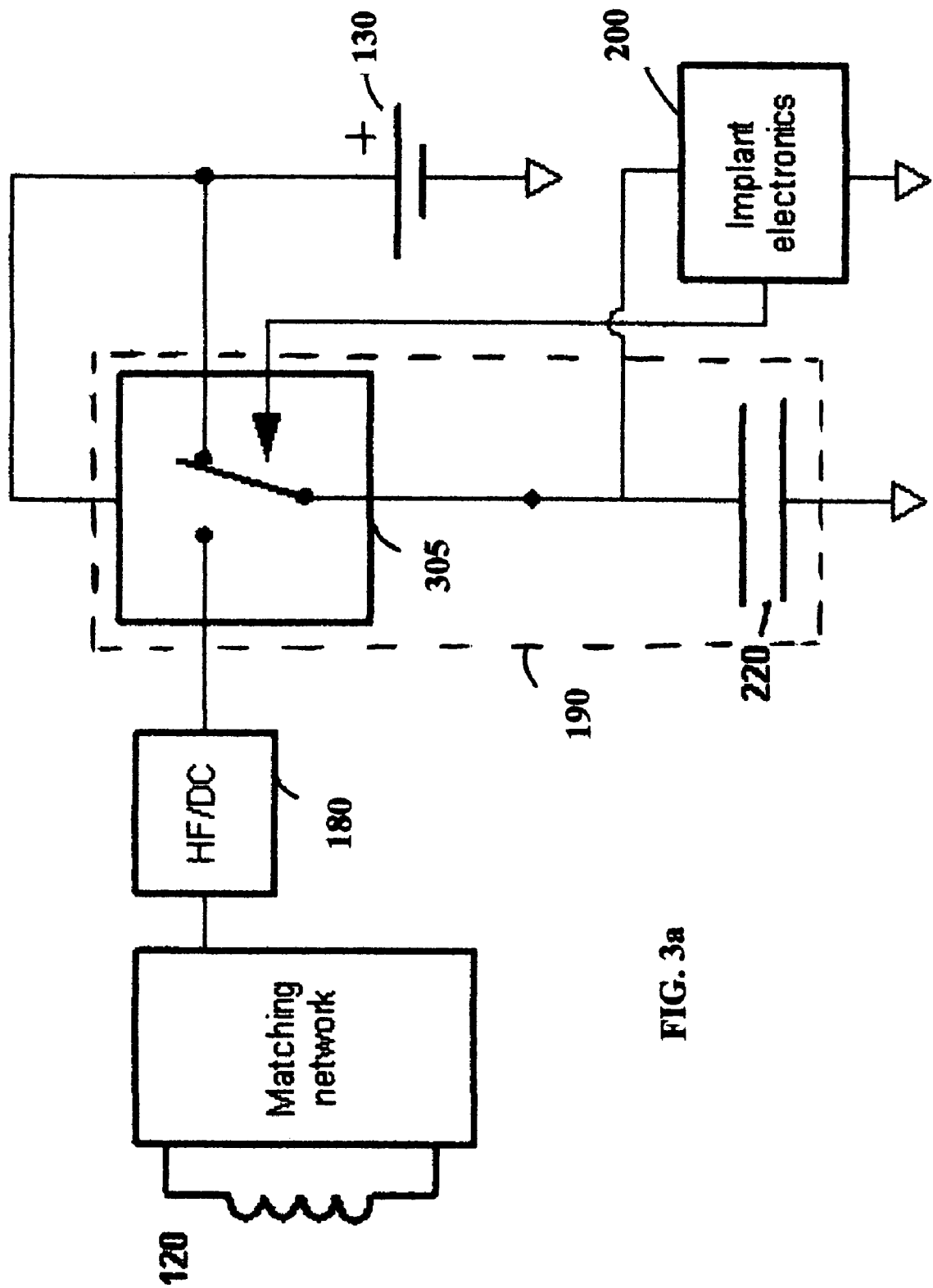
FIG. 3a is a schematic diagram of an exemplary implantable medical device employing active power switching circuitry for use in a TET system.
Figure 3B:
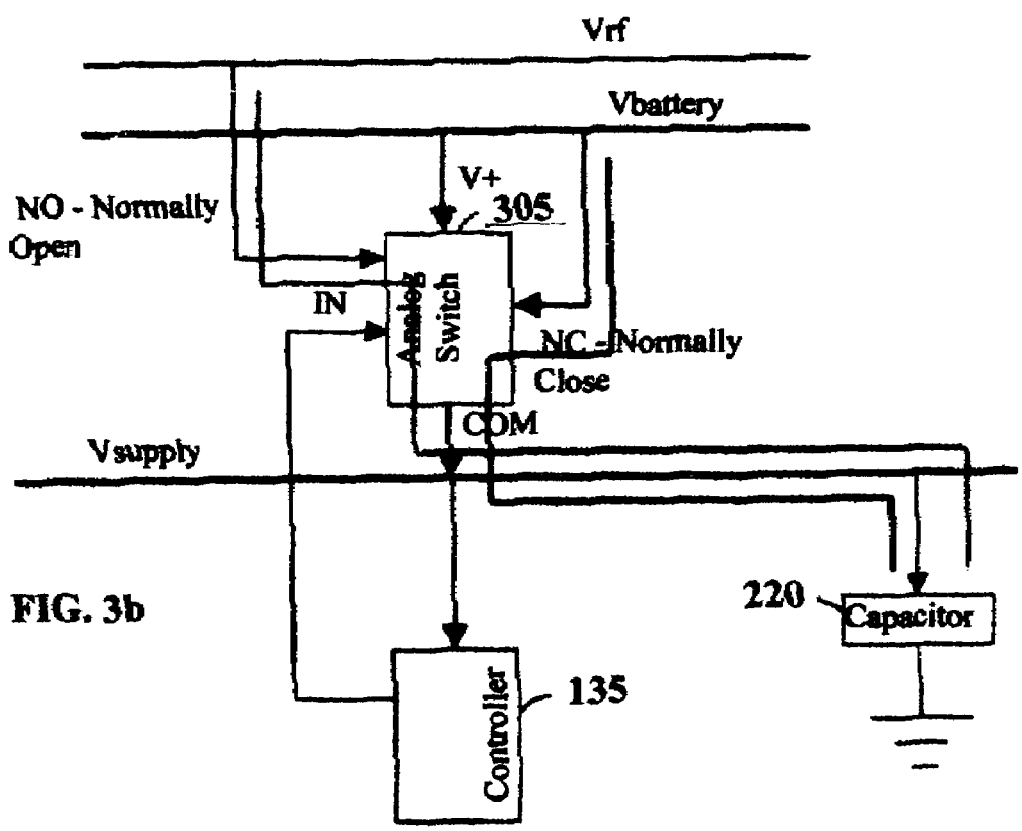

Alternatively, the implantable device may employ active power switching circuitry. FIGS. 3a & 3b show a schematic diagram and flow diagram, respectively, of exemplary active power switching circuitry 190 using an analog switch. In FIG. 3a, implant electronics block 200 generically represents the modulator 170, demodulator 160, microprocessor 135 and any other circuitry associated with the specific functionality of the implant that is not otherwise specifically shown. An analog switch 305 is electrically connected to the RF voltage supply line (Vrf), the battery voltage supply line (Vbattery), and the voltage supply line (Vsupply). Preferably, the analog switch 305 is chosen so as to satisfy the following requirements: relatively low ON resistance; relatively high OFF resistance; relatively low leakage current; relatively low capacitance. In order to bias the internal circuitry, analog switch 305 is continuously powered by the battery 130. Accordingly, as depicted in the flow diagram of FIG. 3b, the battery supply line (Vbattery) is electrically connected to the normally closed (NC) input of the analog switch 305, while the RF voltage supply line (Vrf) is connected to the normally open (NO) input of analog switch 305. The additional drain on the battery in having to continuously power the analog switch increases the overall average current consumption of the components of the implantable medical device.

During RF communication from the external device 100 to the implantable medical device 105, the microprocessor 135 in the implantable medical device determines whether the power supplied by the external RF energy source exceeds that required to energize the implantable medical device and its associated components. If so, microprocessor 135 asserts an enable signal used to trigger analog switch 305 to switch from the internal power source 130 to the external RF energy source. In the absence of RF communication from the external device to the implantable medical device the enable signal from the microprocessor 135 is disabled and the capacitor 220 connected to the Vsupply line is charged automatically from the battery 130. As discussed above, capacitor 220 serves as the stopgap energy supplier while switching from the internal battery to the external RF energy source supplying power to the implantable medical device and its associated components.

Other active components may be employed instead of an analog switch. The use of diodes in accordance with the first embodiment of the invention, however, is preferred over that of the second embodiment using an analog switch due to the increased battery power consumption and larger area footprint on the circuit board when employing an analog switch. Yet still another disadvantage associated with use of an analog switch is that it requires an external logic element (e.g., a microprocessor or controller) for sensing the voltage and controlling the switch. In contrast, the diode configuration is totally passive and not triggered by a microprocessor.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A closed system having dual power supply switching circuitry, comprising:
   an implantable medical device (IMD) disposed interior of a boundary;
   an internal power source for powering the IMD;
   an external device separated from the IMD by and disposed exterior to the boundary, the external device being in telemetric communication with the IMD and generating an external RF energy source during telemetric communication with the IMD; and
   passive power switching circuitry for switching from the internal power source to the external RF energy source during communication from the external device to the IMD when power supplied by the external RF energy source exceeds that required for powering the IMD;
   wherein the power switching circuitry includes a first diode electrically connected to draw power from the external RF energy source, and a second diode electrically connected to draw power from the internal power source;
   wherein the power switching circuitry further comprises a leakage current path via a switch connected in series to a resistor whose resistance is lower than that of the internal power source, wherein in the presence of an external RF voltage when the switch is closed, leakage current flows through the resistor rather than the internal power source.

2. The closed system in accordance with claim 1, wherein the second diode has a relative low voltage drop in the range of between approximately 0.2 V to approximately 0.4 V.

3. The closed system in accordance with claim 1, wherein the power switching circuitry further comprises a capacitor electrically connected to provide power to the IMD while switching the power supply.

4. The closed system in accordance with claim 1, wherein the closed system is a transcutaneous energy transfer system.

5. The closed system in accordance with claim 1, wherein the internal power source is a non-rechargeable battery.

6. A method for switching of a power supply in a closed system including an internal power source used to power an implantable medical device (IMD) separated from an external device by a boundary, comprising the steps of:
generating during communication of the external device with the IMD an external RF energy source; and
during communication from the external device to the IMD when power supplied by the external RF energy source exceeds that required for powering the IMD, switching using passive power switching circuitry from the internal power source to the external RF energy source;
wherein the power switching circuitry includes a first diode electrically connected to draw power from the external RF energy source; and a second diode electrically connected to draw power from the internal power source;
wherein the power switching circuitry further comprises a leakage current path via a switch connected in series to a resistor whose resistance is lower than that of the internal power source, wherein in the presence of an external RF voltage when the switch is closed, leakage current flows through the resistor rather than the internal power source.

7. The method in accordance with claim 6, wherein the second diode has a relative low voltage drop in the range of between approximately 0.2 V to approximately 0.4 V.

8. The method in accordance with claim 6, wherein the power switching circuitry further comprises a capacitor electrically connected to provide power to the IMD while switching the power supply.

9. The method in accordance with claim 6, wherein
the closed system is a transcutaneous energy transfer system.

10. The method in accordance with claim 6, wherein the internal power source is a non-rechargeable battery.

* * * * *